United States Patent
Okamoto et al.

(10) Patent No.: US 8,350,088 B2
(45) Date of Patent: Jan. 8, 2013

(54) GELLING AGENT CONTAINING A FLUOROALKYL DERIVATIVE

(75) Inventors: Hiroaki Okamoto, Ube (JP); Yuki Morita, Ube (JP)

(73) Assignee: National University Corporation Yamaguchi University, Yamaguchi-Shi (JP)

( * ) Notice: Subject to any disclaimer, the term of this patent is extended or adjusted under 35 U.S.C. 154(b) by 294 days.

(21) Appl. No.: 12/808,863

(22) PCT Filed: Nov. 21, 2008

(86) PCT No.: PCT/JP2008/071749
§ 371 (c)(1),
(2), (4) Date: Jun. 17, 2010

(87) PCT Pub. No.: WO2009/078268
PCT Pub. Date: Jun. 25, 2009

(65) Prior Publication Data
US 2012/0184779 A1    Jul. 19, 2012

(30) Foreign Application Priority Data
Dec. 17, 2007    (JP) .................................. 2007-324705

(51) Int. Cl.
*C07C 315/00*    (2006.01)
(52) U.S. Cl. .......................................... 568/28; 568/33
(58) Field of Classification Search ............. 568/33, 568/28
See application file for complete search history.

(56) References Cited

U.S. PATENT DOCUMENTS

| | | | |
|---|---|---|---|
| 5,849,845 A | 12/1998 | Kohler et al. | |
| 6,002,048 A | 12/1999 | Fujii et al. | |
| 6,353,125 B1 * | 3/2002 | Wachtler et al. | 558/54 |

FOREIGN PATENT DOCUMENTS

| | | |
|---|---|---|
| JP | 8-231842 A | 9/1996 |
| JP | 10-175901 A | 6/1998 |
| JP | 2007-191626 A | 8/2007 |
| WO | WO 2007/083843 A1 | 7/2007 |

OTHER PUBLICATIONS

McAdams, C.L. et al, The Influence of Structure on Dissolution Inhibition for Novolac-Based Photoresists: Adaption of the Probabilistic Aprroach, ACS Symposium Series; Micro- and Nanopatterning Polymers, 1998; Chapter 22; 292-305.*
Napoli, M., Journal of Fluorine Chemistry, 79 (1996) 59-69.*
Napoli, M. et al, Journal of Fluorine Chemistry, 85 (1997) 163-167.*
Cheng, L. et al, Journal of Physical chemistry, 1991, 95, 10631-10643.*
International Search Report, dated Feb. 3, 2009, issued in corresponding PCT/JP2008/071749.
Napoli et al., "Synthesis of F(CF2)8(CH2)8H and Gel Phase Formation From Its Solutions in Homologous Alcohols", Journal of Fluorine Chemistry, vol. 110, 2001, pp. 47-58, Elsevier.

* cited by examiner

*Primary Examiner* — Johann Richter
*Assistant Examiner* — Pancham Bakshi
(74) *Attorney, Agent, or Firm* — Birch, Stewart, Kolasch & Birch, LLP

(57) ABSTRACT

To provide a gelling agent containing a fluoroalkyl derivative, a small amount of which can gelatinize or solidify various organic solvents.
The gelling agent for organic liquids contains a fluoroalkyl derivative represented by the following formula:

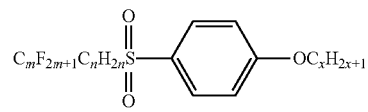

wherein each of m, n and x is a positive integer.

3 Claims, 1 Drawing Sheet

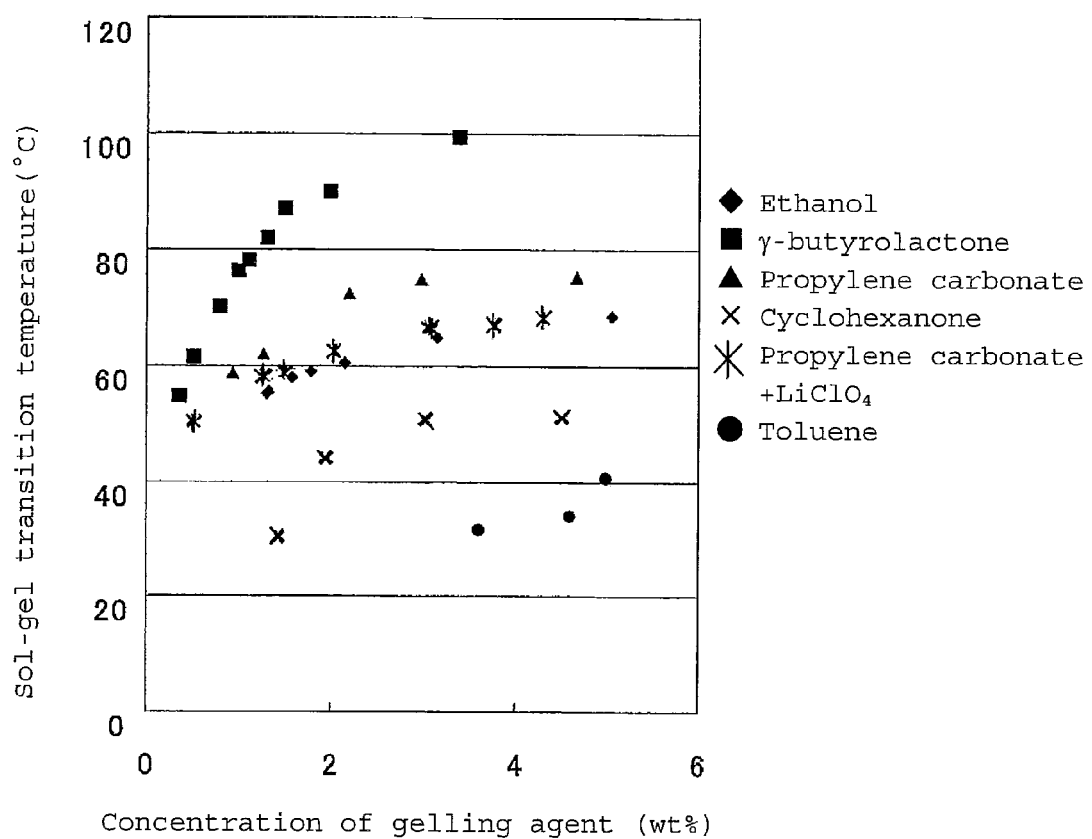

GELLING AGENT CONTAINING A FLUOROALKYL DERIVATIVE

TECHNICAL FIELD

The present invention relates to a novel compound. It relates to a gelling agent comprising the compound and capable of gelatinizing organic solvent(s).

BACKGROUND ART

Heretofore, low-molecular weight and high-molecular weight organic gelling agents have been used to solidify organic liquids in the fields of battery electrolytes, coating compositions, inks, lubricant oils, agriculture, fishery, cosmetics, medicinal goods, fibers, resins, polymers, rubbers and metals. Most of the organic gelling agents are known as low-molecular weight compounds having a hydrogen bonding functional group (such as an amino group, amide group or urea) in their molecule and high-molecular weight compounds having a 3-D network structure in their molecule. Although the development of the former compounds was relatively later than the development of the latter compounds, there are known dialkylurea derivatives (refer to JP-A 8-231942) and perfluoroalkyl derivatives (refer to JP-A 2007-191626 and J. Fluorine Chem. 111, 47-58 (2001)).

However, the above compounds have such problems that there are a small number of types of solvents able to be gelatinized therewith, it is difficult to stabilize gel therewith, and a relatively large amount of a gelling agent is required for the gelation of an organic electrolytic solution containing an electrolyte in high concentration.

DISCLOSURE OF THE INVENTION

It is therefore an object of the present invention to provide a novel compound, a small amount of which can gelatinize or solidify various organic solvents and a gelling agent comprising the compound.

Other objects and advantages of the present invention will become apparent from the following description.

According to the present invention, the above object and advantage of the present invention are attained by a compound represented by the following formula (1):

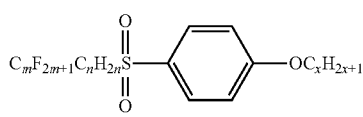

(wherein each of m, n and x is a positive integer).

According to the present invention, the above object and advantage of the present invention are attained by a gelling agent for organic liquids, which comprises the above compound.

BRIEF DESCRIPTION OF THE DRAWINGS

FIG. 1 is a graph showing the relationship between the concentration of the compound (1) of the present invention produced in Example 1 and the temperature at which gel is changed into sol.

BEST MODE FOR CARRYING OUT THE INVENTION

The present invention is a novel compound represented by the following formula (1).

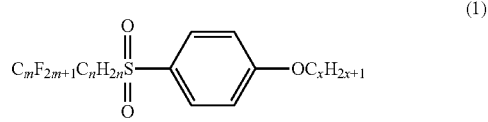

(wherein each of m, n and x is a positive integer.)

The compound of the above formula (1) is particularly useful as a gelling agent. The compound of the formula (1) is advantageously used to gelatinize a large number of organic solvents such as alcohols including ethanol, propanol, butanol and octanol, esters including methyl acetate, ethyl acetate, propyl acetate and butyl acetate, ketones including dimethyl ketone, diethyl ketone and methyl ethyl ketone, carbonates including propylene carbonate and butylene carbonate, lactones including γ-butyrolactone and γ-valerolactone, hydrocarbons including octane, cyclohexane, benzene, toluene and xylene(s), nitriles including acetonitrile, other solvents, mixtures thereof and solvents obtained by dissolving $LiClO_4$, $LiPF_6$, $LiBF_4$, or ionic liquids such as ionic substances represented by the following formulas in these organic solvents.

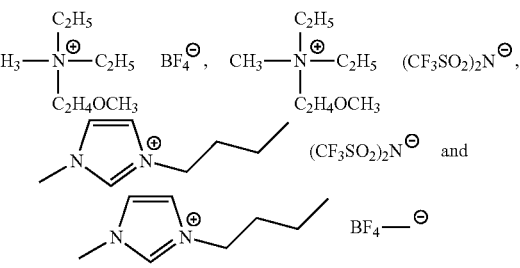

The amount of the compound is relatively small, for example, 0.5 to 5 wt %, preferably 1 to 3 wt %. When the gelling agent is added in this small amount, it can gelatinize an organic solvent.

As preferred examples of the above compound, in the above formula (1), "m" is preferably 5 to 15, more preferably 6 to 12, "n" is preferably 1 to 6, more preferably 2, and "x" is preferably 1 to 12, more preferably 6 to 8.

The compound of the present invention can be produced through known reaction(s).

The following examples are provided to further illustrate the present invention.

EXAMPLES

Example 1

The compound (1) of the present invention was synthesized based on the following scheme.

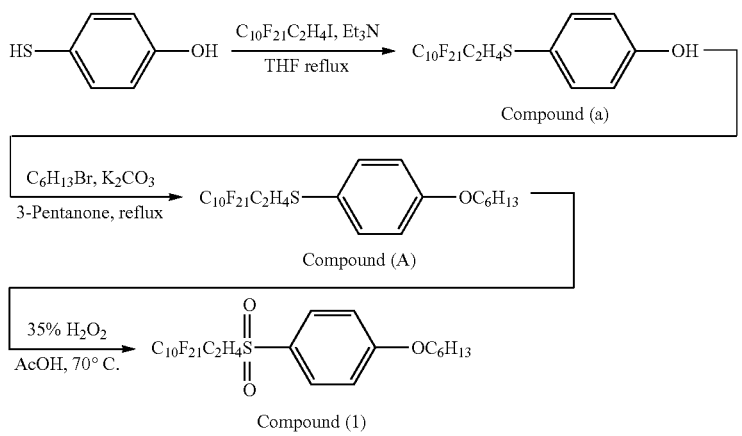

Synthesis of Compound (A)

The compound (A) was synthesized by the following procedure in accordance with the method described in JP-A 2007-191626 which was filed by the Applicant of this application. 1.5 equivalents of triethylamine ($Et_3N$) and 1.0 equivalent of $C_{10}F_{21}C_2H_4I$ were added to a THF (tetrahydrofuran) solution containing 1.86 g of 4-mercaptophenol and refluxed for 24 hours. Thereafter, 1N hydrochloric acid was added, and the reaction product was extracted with ether, rinsed with water (twice) and brine and dried with magnesium sulfate. The solvent was distilled off, and the residue was purified by silica gel column chromatography to obtain a compound (a) (5.89 g, yield of 59%).

Compound (a); $^1$HNMR ($CDCl_3$) δ=2.33 (2H, m), 2.99 (2H, m), 4.90 (1H, s), 6.81 (2H, d, J=8.9 Hz), 7.31 (2H, d, J=8.9 Hz) ppm IR (KBr)=1151, 1209, 3400 $cm^{-1}$ 1.0 equivalent of 1-bromohexane and 1.5 equivalents of potassium carbonate were added to a 3-pentanone solution containing 0.5 g of the compound (a) obtained from the above reaction and refluxed for 20 hours. A precipitate which separated out from the reaction solution was separated by filtration, the solvent of the filtrate was distilled off, and the filtrate was purified by silica gel column chromatography to obtain a compound (A) (0.5 g, yield of 76%).

IR (KBr)=1147, 1201, 1244, 2917 $cm^{-1}$

Compound (A); $^1$HNMR (270 MHz, $CDCl_3$) δ=0.88 (3H, t, J=6.8 Hz), 1.22-1.45 (6H, m), 1.75 (2H, quin, J=6.9 Hz), 2.51 (2H, m), 2.96 (2H, m), 3.96 (2H, t, J=6.6 Hz), 6.86 (2H, d, J=8.9 Hz), 7.36 (2H, d, J=8.9 Hz) ppm The above synthesis was repeated to obtain an amount required in the following experiment of the compound (A) so as to synthesize a compound (1) which is the gelling agent of the present invention by the following procedure.

Synthesis of Compound (1)

1.0 g of the compound (A) was added to a solution (70 ml) of glacial acetic acid (AcOH), and 0.5 ml of a hydrogen peroxide solution (35%) was added to the resulting solution and stirred at 70° C. for 12 hours. After agitation, the obtained solution was gradually cooled to room temperature, 150 ml of ether and 200 ml of water were added, and the resulting mixture was transferred to a separating funnel to remove a water phase. An organic phase was washed with 100 ml of water, 100 ml of an aqueous solution of saturated sodium bicarbonate and saturated brine sequentially. The organic phase was dried with $MgSO_4$. After $MgSO_4$ was separated by filtration, the solvent of the organic phase was removed under reduced pressure. The residue was purified by silica gel chromatography to obtain 0.7 g of the compound (1).

mp=126-131° C.

IR (KBr Disc) v=1092, 1290, 1209, 2936 $cm^{-1}$ $^1$HNMR ($CDCl_3$) δ=0.91, (3H, t, J=6.9 Hz), 1.28-1.40 (6H, m), 1.82 (2H, qui., J=7.0 Hz), 2.57 (2H, m), 3.29 (2H, t, J=8.2 Hz), 4.04 (2H, t, J=6.6 Hz), 7.04 (2H, d, J=8.0 Hz), 7.84 (2H, d, J=8.0 Hz) ppm molecular weight (calculated value): 788

Experimental Value

EI-MS spectrum: m/z 788 (M), m/z 769 (M-F), m/z 705 (M-$C_6H_{11}$) m/z 241 (M-$C_2H_4C_{10}F_{21}$)

CI-MS spectrum: m/z 789 (M+1)

After an organic solvent was added to the compound (1) obtained as described above, heated and stirred to dissolve it, the resulting solution was gradually cooled to check its gelation with the eye. This gel was heated again to measure a temperature at which this became a solution (sol).

The sol-gel transition temperatures when ethanol, γ-butyrolactone, propylene carbonate, cyclohexanone and propylene carbonate (containing 1M $LiClO_4$) were used as the organic solvent are shown in Table 1. These results are shown in FIG. 1.

FIG. 1 is a graph showing the relationship between the concentration of the gelling agent and the temperature at which gel is changed into sol. As obvious from FIG. 1, a small amount of the gelling agent of the present invention can gelatinize an organic solvent.

TABLE 1

| Minimum concentration of gelling agent (wt %) | Sol-gel transition temperature |
|---|---|
| Solvent (ethanol) | |
| 5.05 | 68.5 |
| 3.15 | 64.9 |
| 2.15 | 60.5 |
| 1.78 | 59.0 |
| 1.57 | 58.0 |
| 1.3 | 55.1 |
| Toluene | |
| 4.99 | 40.7 |
| 4.59 | 34.0 |
| 3.60 | 31.6 |

TABLE 1-continued

| Minimum concentration of gelling agent (wt %) | Sol-gel transition temperature |
|---|---|
| Propylene carbonate | |
| 4.66 | 75.3 |
| 2.98 | 74.9 |
| 2.20 | 72.5 |
| 1.26 | 62.0 |
| 0.93 | 58.8 |
| Cyclohexanone | |
| 4.50 | 51.3 |
| 3.03 | 50.8 |
| 1.95 | 44.2 |
| 1.42 | 30.3 |
| γ-Butyrolactone | |
| 3.39 | 99.5 |
| 1.99 | 90.1 |
| 1.49 | 87.2 |
| 1.30 | 82.0 |
| 1.10 | 78.1 |
| 0.99 | 76.3 |
| 0.79 | 70.1 |
| 0.50 | 61.5 |
| 0.36 | 54.7 |
| Propylene carbonate + $LiClO_4$ | |
| 4.30 | 68.4 |
| 3.77 | 67.3 |
| 3.08 | 66.9 |
| 2.04 | 62.7 |
| 1.49 | 59.0 |
| 1.29 | 58.3 |
| 0.50 | 50.5 |

The gelling agent containing a fluoroalkyl derivative of the present invention can gelatinize or solidify an organic solvent even when it is added in a small amount and is excellent in the stability of its gelatinized substance, thereby providing stable gel.

The gelling agent of the present invention can be easily produced and used in processing fields such as battery electrolytes, coating compositions, inks, lubricant oils, agriculture, fishery, cosmetics, medicinal goods, fibers, resins, polymers, rubbers and metals.

The invention claimed is:

1. A compound represented by the following formula (I):

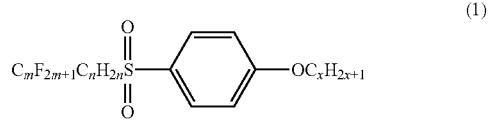

(1)

wherein each of m, n and x is a positive integer.

2. A gelling agent for organic liquids, which comprises the compound of claim 1.

3. A method for gelatinizing an organic liquid, comprising the step of:

combining the organic liquid with the compound of claim 1 in order to gelatinize the organic liquid.

* * * * *